United States Patent
Vitello et al.

(10) Patent No.: US 9,821,152 B1
(45) Date of Patent: Nov. 21, 2017

(54) CLOSURE ASSEMBLY

(71) Applicants: Jonathan J. Vitello, Ft. Lauderdale, FL (US); Patrick Vitello, Ft. Lauderdale, FL (US); William Gil de Montes, Pembroke Pines, FL (US)

(72) Inventors: Jonathan J. Vitello, Ft. Lauderdale, FL (US); Patrick Vitello, Ft. Lauderdale, FL (US); William Gil de Montes, Pembroke Pines, FL (US)

(73) Assignee: Medical Device Engineering, LLC., Pompano Beach, FL (US)

( * ) Notice: Subject to any disclaimer, the term of this patent is extended or adjusted under 35 U.S.C. 154(b) by 660 days.

(21) Appl. No.: 14/196,369

(22) Filed: Mar. 4, 2014

Related U.S. Application Data

(60) Provisional application No. 61/772,094, filed on Mar. 4, 2013.

(51) Int. Cl.
*A61M 39/20* (2006.01)
*A61M 39/10* (2006.01)

(52) U.S. Cl.
CPC ........ *A61M 39/20* (2013.01); *A61M 39/1011* (2013.01)

(58) Field of Classification Search
CPC .... A61M 2005/3104; A61M 2005/312; A61M 5/5086; A61M 39/20; A61M 39/1011
See application file for complete search history.

(56) References Cited

U.S. PATENT DOCUMENTS

| | | |
|---|---|---|
| 1,970,631 A | 8/1934 | Sherman |
| 2,834,346 A | 5/1958 | Adams |
| 2,888,015 A | 5/1959 | Hunt |
| 3,245,567 A | 4/1966 | Knight |
| 3,364,890 A | 1/1968 | Andersen |
| 3,706,307 A | 12/1972 | Hasson |
| 3,747,751 A | 7/1973 | Miller et al. |
| 3,905,375 A | 9/1975 | Toyama |
| 4,216,585 A | 8/1980 | Hatter |
| 4,216,872 A | 8/1980 | Bean |
| 4,313,539 A | 2/1982 | Raines |
| 4,420,085 A | 12/1983 | Wilson et al. |
| 4,430,077 A | 2/1984 | Mittleman et al. |
| 4,457,445 A | 7/1984 | Hanks et al. |
| 4,521,237 A | 6/1985 | Logothetis |

(Continued)

*Primary Examiner* — Imani Hayman
(74) *Attorney, Agent, or Firm* — Malloy & Malloy, P.L.

(57) ABSTRACT

A closure assembly for a syringe having a nozzle or access portion and a discharge port including a closure cap or syringe cap having a access engaging portion removably connectible in flow restricting relation to the discharge port. A connecting structure is mounted on the access engaging portion and disposed and configured to define an interactive engagement with an attachment structure of the nozzle or access portion of the syringe. Structural and operative features of the connecting structure enable a "push-on connection" of the closure cap or syringe cap to the nozzle or access portion and a "rotate-off disconnection" of the closure cap or syringe cap from the nozzle or access portion. The closure cap or syringe cap may be used independently of or in combination with an end cap and an included indicator member, wherein the combination closure cap or syringe cap and end cap define a tamper evident cap for the syringe.

30 Claims, 11 Drawing Sheets

(56) References Cited

U.S. PATENT DOCUMENTS

| | | |
|---|---|---|
| 4,530,697 A | 7/1985 | Kuhlemann et al. |
| 4,571,242 A | 2/1986 | Klein et al. |
| 4,589,171 A | 5/1986 | McGill |
| 4,667,837 A | 5/1987 | Vitello et al. |
| 4,693,707 A | 9/1987 | Dye |
| 4,726,483 A | 2/1988 | Drozd |
| 4,743,231 A | 5/1988 | Kay et al. |
| 4,760,847 A | 8/1988 | Vaillancourt |
| 4,832,695 A | 5/1989 | Rosenberg et al. |
| 4,834,706 A | 5/1989 | Beck et al. |
| 4,844,906 A | 7/1989 | Hermelin et al. |
| 4,919,285 A | 4/1990 | Roof et al. |
| 5,009,323 A | 4/1991 | Montgomery et al. |
| 5,049,129 A | 9/1991 | Zdeb et al. |
| 5,135,496 A | 8/1992 | Vetter et al. |
| 5,165,560 A | 11/1992 | Ennis, III et al. |
| 5,230,429 A | 7/1993 | Etheredge, III |
| 5,292,308 A | 3/1994 | Ryan |
| 5,328,466 A | 7/1994 | Denmark |
| 5,328,474 A | 7/1994 | Raines |
| 5,356,380 A | 10/1994 | Hoekwater et al. |
| 5,458,580 A | 10/1995 | Hajishoreh |
| 5,468,224 A | 11/1995 | Souryal |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,624,402 A | 4/1997 | Imbert |
| 5,702,374 A | 12/1997 | Johnson |
| 5,776,124 A | 7/1998 | Wald |
| 5,785,691 A | 7/1998 | Vetter et al. |
| 5,807,343 A | 9/1998 | Tucker et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,989,227 A | 11/1999 | Vetter et al. |
| 6,000,548 A | 12/1999 | Tsals |
| 6,021,824 A | 2/2000 | Larsen et al. |
| 6,027,482 A | 2/2000 | Imbert |
| 6,068,614 A | 5/2000 | Kimber et al. |
| 6,126,640 A | 10/2000 | Tucker et al. |
| 6,190,364 B1 | 2/2001 | Imbert |
| 6,193,688 B1 | 2/2001 | Balestracci et al. |
| 6,196,998 B1 | 3/2001 | Jansen et al. |
| 6,280,418 B1 | 8/2001 | Reinhard et al. |
| 6,322,543 B1 | 11/2001 | Singh et al. |
| 6,338,200 B1 | 1/2002 | Baxa et al. |
| 6,375,640 B1 | 4/2002 | Teraoka |
| 6,394,983 B1 | 5/2002 | Mayoral et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,726,652 B2 | 4/2004 | Eakins et al. |
| 6,726,672 B1 | 4/2004 | Hanly et al. |
| 6,764,469 B2 | 7/2004 | Broselow |
| 6,821,268 B2 | 11/2004 | Balestracci |
| 6,921,383 B2 | 7/2005 | Vitello |
| 6,942,643 B2 | 9/2005 | Eakins et al. |
| 7,141,286 B1 | 11/2006 | Kessler et al. |
| 7,182,256 B2 | 2/2007 | Andreasson et al. |
| 7,374,555 B2 | 5/2008 | Heinz et al. |
| 7,404,500 B2 | 7/2008 | Marteau et al. |
| 7,425,208 B1 | 9/2008 | Vitello |
| 7,437,972 B2 | 10/2008 | Yeager |
| 7,588,563 B2 | 9/2009 | Guala |
| 7,632,244 B2 | 12/2009 | Buehler et al. |
| 7,641,636 B2 | 1/2010 | Moesli et al. |
| 7,735,664 B1 | 6/2010 | Peters et al. |
| 7,762,988 B1 | 7/2010 | Vitello |
| 7,802,313 B2 | 9/2010 | Czajka |
| 7,918,830 B2 | 4/2011 | Langan et al. |
| 8,079,518 B2 | 12/2011 | Turner et al. |
| 8,091,727 B2 | 1/2012 | Domkowski |
| 8,140,349 B2 | 3/2012 | Hanson et al. |
| 8,328,082 B1 | 12/2012 | Bochenko et al. |
| 8,348,895 B1 | 1/2013 | Vitello |
| 8,353,869 B2 * | 1/2013 | Ranalletta ............... A61M 5/50 604/111 |
| 8,443,999 B1 | 5/2013 | Reinders |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| 8,702,674 B2 | 4/2014 | Bochenko |
| 8,864,021 B1 | 10/2014 | Vitello |
| 8,864,707 B1 | 10/2014 | Vitello |
| 8,864,708 B1 | 10/2014 | Vitello |
| 8,945,082 B2 | 2/2015 | Geiger et al. |
| 9,101,534 B2 | 8/2015 | Bochenko |
| 9,199,042 B2 | 12/2015 | Farrar et al. |
| 9,199,749 B1 | 12/2015 | Vitello |
| 9,272,099 B2 | 3/2016 | Limaye et al. |
| 9,311,592 B1 | 4/2016 | Vitello |
| 9,336,669 B2 | 5/2016 | Bowden et al. |
| 9,402,967 B1 | 8/2016 | Vitello |
| 9,463,310 B1 | 10/2016 | Vitello |
| 2002/0023409 A1 | 2/2002 | Py |
| 2002/0133119 A1 | 9/2002 | Eakins et al. |
| 2003/0183547 A1 | 10/2003 | Heyman |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2006/0084925 A1 | 4/2006 | Ramsahoye |
| 2007/0106234 A1 | 5/2007 | Klein |
| 2007/0142786 A1 | 6/2007 | Lampropoulos et al. |
| 2008/0068178 A1 | 3/2008 | Meyer |
| 2009/0149815 A1 | 6/2009 | Kiel et al. |
| 2010/0084403 A1 | 4/2010 | Popish et al. |
| 2010/0126894 A1 | 5/2010 | Koukol et al. |
| 2011/0044850 A1 | 2/2011 | Solomon et al. |
| 2011/0046550 A1 | 2/2011 | Schiller et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2014/0155868 A1 | 6/2014 | Nelson et al. |
| 2015/0305982 A1 | 10/2015 | Bochenko |
| 2016/0144119 A1 | 5/2016 | Limaye et al. |
| 2016/0158449 A1 | 6/2016 | Limaye et al. |
| 2016/0176550 A1 | 6/2016 | Vitello et al. |
| 2016/0328586 A1 | 11/2016 | Bowden et al. |

\* cited by examiner

CLOSURE ASSEMBLY

CLAIM OF PRIORITY

The present application is based on and a claim of priority is made under 35 U.S.C. Section 119(e) to a provisional patent application that is currently in the U.S. Patent and Trademark Office, namely, that having Ser. No. 60/772,094 and a filing date of Mar. 4, 2013, and which is incorporated herein by reference.

BACKGROUND OF THE INVENTION

Field of the Invention

This invention is directed to a closure assembly for a fluid loaded syringe or other medical device/container which includes structural features allowing it to be used independently, as a closure cap or syringe cap, connected in flow restricting relation to the access portion of a medical container or like device including, but not limited to a syringe. Alternatively, the closure assembly may be used in combination with an end cap and indicator member, and thereby serve as a part of a tamper evident cap (TEC) for the medical device/container or syringe. When used in either capacity, the structural and operative features of the closure cap or syringe cap provide for divergent connecting/disconnecting procedures including a push-on or snap-on type connection and a rotate-off type disconnection.

Description of the Related Art

In hospitals or other medical care facilities, it is very common for medical doctors and other authorized medical personnel to order that a patient be given a drug or medication by injection. In fact, it is currently estimated that more than 16 billion injections are administered on a worldwide basis in any given year.

As a result, it is becoming relatively common in hospital settings for a number of syringes to be pre-loaded or filled by a pharmacist, or other authorized personnel within a hospital or similar facility, at an appropriate location for subsequent dispensing to one or more patients. The pharmacy or other location where syringes are filled can and often will be located in a remote part of the hospital, relative to the patient care area where the injection is to be administered. In some cases, the loading of syringes occurs in another building or facility entirely, often referred to as "third party pharmacies." This may even be a growing trend among hospitals to limit certain costs. Regardless, a syringe filling station at a large medical facility may resemble a factory, from which drug loaded syringes are delivered to a large number of nurse's stations in multiple hospital or medical buildings. Because many nurse's stations are typically remotely located from a syringe filling station, a loaded syringe is quite often given to another person for delivery to a nurse's station, for subsequent dosing of the patient by qualified personnel. From the foregoing, it may be understood that during the course of loading a syringe with a drug, and delivering the loaded syringe to a nurse's station or to a patient, the syringe can easily be handled by numerous personnel.

Also, and especially in the case of a very expensive drug or an addictive drug, there is some danger that a pre-loaded syringe will be tampered with by a person seeking to improperly gain access to the drug. A resulting danger also exists relating to the possibility of inappropriately substituting saline solution or some other unauthorized substance for the intended medication originally loaded into the syringe. Thus, the growing use of syringes which are pre-loaded with a drug presents another problem in that it is important to know if the pre-loaded syringe has, or has not, been tampered with, exposed to contamination or otherwise compromised.

The benefits of using a pre-filled syringe and the ability to readily determine whether or not it has been tampered with, are abundantly clear. At the same time, however, drugs and medications are specific to each particular patient's disorder or disease being treated, and in addition, interactions between drugs and medications given to a patient incorrectly can have serious and deadly consequences. It is, therefore, important to know that a particular medication being injected is, in fact, the drug that was prescribed by the treating physician, and that it has not been replaced by another compound. Moreover, some drugs can have harmful effects in large doses. Accordingly, it is also important to ensure that the proper dosage is followed, as prescribed. Since pre-filled syringes are prepared in advance of being delivered and used, they may be loaded carefully by a pharmacist or other similarly qualified individual to ensure the appropriate medication and dose is prepared. This reduces errors on injection by nurses or physicians who may be in a stressful or time-sensitive situation and may not have the luxury of verifying the correct medication or measuring out a dose, particularly small doses, from a source vial.

There has historically been a problem, however, of knowing if a sealed, preloaded syringe has, or has not, been compromised by it being tampered with or if it might otherwise have a loss of sterility or have become contaminated. This and related types of problems have been described in the inventor's own previously granted U.S. Pat. No. 4,667,837 and in other patents, such as U.S. Pat. No. 5,328,474. Despite attempts in the past to prevent unauthorized access to syringe(s) pre-loaded with a drug or medication, it is understood that some problems continue to exist in this field of art and there remains an ongoing need for further improvements, despite the introduction of inventive products according to the above-noted two patents and others.

For instance, there remain problems of manufacturing such products in a manner which is relatively easy and inexpensive, as well as some problems involved with the assembly and placement onto a drug loaded syringe, such as at a drug filling station. Other problems exist relative to maintaining the sterility during storage at the manufacturing facility of some caps for syringes, and during transport of them to a hospital or other medical facility, during storage of them at a hospital or other medical facility, including any transport to a nursing station and ultimately, to a patient care area.

Accordingly, there is a need in this area for an improved closure assembly having the structural versatility to be used as a closure cap or closure cap or syringe cap or as a tamper evident cap (TEC), wherein the proposed closure assembly can be used in either capacity with standard or conventional pre-loaded syringe in a manner which overcomes problems and or disadvantages of the type set forth above. The development of any such improved closure assembly would preferably offer certain features such as, but not limited to, the cooperative structuring of a connecting structure which enables the proposed closure assembly to be connected to and removed from the nozzle or access portion of a pre-loaded syringe by a "push-on" connection and a "rotate-off" disconnection. In addition, if any such improved, closure assembly were developed, it would ideally be structurally and operatively reliable, while still remaining relatively easy and cost effective to make and assemble, in order to facilitate widespread use and acceptance through out the medical profession.

From the foregoing, one might appreciate that the present invention seeks to address such problems and others associated with closure assemblies for preloaded syringes including, but not limited to, tamper evident caps and luer lock caps during their manufacture, assembly and/or use.

SUMMARY OF THE INVENTION

The present invention is directed to a closure assembly for a standard syringe, a pre-loaded syringe or other medical device/container having an access portion or structure which includes a discharge port. For purposes of clarity, in describing the structural and operative features of the present invention, primary reference will be made to a conventional or standard syringe 11 as disclosed in the prior art representation of FIG. 1. However, it is emphasized that the closure assembly of the present invention may be used with a variety of different medical containers or like medical devices in which a fluid is or may be stored and/or retained and which includes an access portion and a discharge port through which a contained fluid may be dispensed. As such, the syringe 11 typically includes a barrel 1 and a nozzle or access portion 2. The barrel 1 comprises an elongate interior chamber disposed in fluid communication with an axial passageway or channel 3 on the interior of the nozzle or access portion tube 2' or like nozzle or access portion 2, which may comprise a portion of a luer type fitting. The channel 3 is to be considered a portion of the nozzle or access portion 2 and terminates distally at an opening or discharge port 4. A piston 5 slides within the barrel and includes a head 6 provided with a circumferential gasket means 7. When assembled, the end face 9 of the head 6 of the piston confronts the interior end of the channel 3 and closes the discharge port 4. The piston also includes a push rod or plunger 8 that is connected to the head 6 and dimensioned to pass into the barrel 1. Accordingly, the access portion 2 preferably includes an attachment structure 3', such as a ribbed or at least partially threaded interior surface.

As emphasized hereinafter, the structural and operative versatility of the preferred embodiments of the closure assembly allow it to be used as a closure cap or closure cap or syringe cap connected in flow restricting relation to a discharge port, such as at 4 of a syringe, such as at 11. Alternatively, the closure cap or closure cap or syringe cap may be used in combination with an end cap and an included indicator member, wherein this combination defines a tamper evident cap (TEC).

As also explained in greater detail hereinafter, the structural and operative features of the closure cap or closure cap or syringe cap, facilitate a connecting procedure onto a syringe, and in some embodiments, what could be considered a divergent connecting/disconnecting procedure. More specifically, the closure cap or closure cap or syringe cap may be manipulated to accomplish a "push-on" or "snap on" manner of connection and a "rotate-off disconnection." In addition, the versatile structural features of the closure cap or closure cap or syringe cap also provide for a "rotate-on" connection, as well as "rotate-off" disconnection as preferred.

Therefore, the closure cap or closure cap or syringe cap of the closure assembly includes a access engaging portion removably connectible in surrounding, flow restricting relation to the discharge port 4 of the nozzle or access portion 2 of a syringe 11 of the type generally represented in FIG. 1, as set forth above. Structural features which facilitate the versatile operability of the closure cap or closure cap or syringe cap include a connecting structure mounted on the access engaging portion cooperatively structured to interactively engage an attachment structure of the nozzle or access portion of the syringe. This cooperative structuring of the access engaging portion with the attachment structure enables the aforementioned push-on or snap-on connection and rotate-off disconnection and/or rotate-on connection and rotate-off disconnection.

In at least one preferred embodiment, the connecting structure comprises a segmented thread structure including a plurality of protrusions formed on an exterior surface or wall surface of the access engaging portion. Moreover, the plurality of protrusions are collectively disposed into an array comprising a predetermined configuration which facilitates both the push-on connection and/or rotate-off disconnection. The divergent connection/disconnection capabilities of the closure cap or closure cap or syringe cap relative to the nozzle or access portion 2 and discharge port 4 of a syringe 11 is further defined by the plurality of protrusions collectively comprising a substantially helical configuration. This helical configuration of the protrusions, as well as the protrusions being cooperatively dimensioned with the attachment structure 3' of the nozzle or access portion 2, facilitates a rotational, threaded attachment there between.

Additional versatility of the closure cap or closure cap or syringe cap is provided by the inclusion of a flexible construction of the access engaging portion. Such a flexible construction is sufficient to accomplish at least a predetermined degree of flexure of the access engaging portion sufficient to facilitate or provide for the "push-on" or "snap-on" connection of the closure cap or closure cap or syringe cap on to the nozzle or access portion 2 of the syringe 11. The "push-on" or "snap-on" connection is preferably accomplished by an axial alignment between the nozzle or access portion and the closure cap or closure cap or syringe cap and a substantially linearly directed force being exerted on either the closure cap or closure cap or syringe cap or the syringe 11 towards one another. The use of the "push-on" connection may be especially preferred and more efficient in a manufacturing or assembling facility where a large number of closure assemblies are attached to an equivalently large number of preloaded syringes. In such an environment, the closure cap or closure cap or syringe cap (or closure cap or closure cap or syringe cap and end cap TEC's combination) may be fixedly maintained on a stable platform thereby enabling the syringe to be aligned therewith and having a substantially linear force being applied thereto. The result will be the aforementioned "push-on" or "snap-on" attachment of the closure cap or closure cap or syringe cap and the nozzle or access portion of the syringe. Alternatively, the syringe may be similarly disposed in a stable position or orientation, thereby enabling the closure cap or closure cap or syringe cap to be aligned with the nozzle or access portion thereof and being linearly pushed on to the nozzle or access portion. The aforementioned push-on connection between the closure cap or closure cap or syringe cap and the nozzle or access portion of the syringe will be the result.

The aforementioned rotate-off disconnection comprises a relative rotational engagement between the closure cap or closure cap or syringe cap and the attachment structure of the nozzle or access portion. Due to the fact that the protrusions may be formed into the substantially helical configuration, the closure cap or closure cap or syringe cap may be rotationally threaded on to or rotationally unthreaded from the nozzle or access portion through the rotational engagement between the plurality of protrusions and the attachment structure associated with the nozzle or access portion of the syringe. As described above and as is commonly utilized, the attachment structure 3' of the syringe 11 may include and be at least partially defined by an internally threaded or substantially similarly configured surface surrounding the discharge port 4 and/or nozzle tube 2'.

Additional structural features of one or more preferred embodiments of the closure assembly of the present invention include the aforementioned flexible construction of the access engaging portion of the closure cap or closure cap or syringe cap. Moreover, this flexible construction comprises at least one but preferably a plurality of hinge structures integrally formed into the access engaging portion of the closure cap or closure cap or syringe cap. Further, at least one but more practically each of the plurality of hinge structures may be defined by a "living hinge". In general or conventional terms, a living hinge is a thin flexible hinge made from the same material as two comparatively rigid pieces which it serves to interconnect. As such, the thin flexible hinge segment of membrane is integrally formed with the two comparatively rigid pieces which it interconnects thereby facilitating an at least partial hinged movement there between and a flexure of the access engaging portion. Accordingly, the flexible construction at least partially defined by the plurality of living hinges is operable and sufficient to accomplish a predetermined flexure of the access engaging portion at least during the push-on connection.

The fixed or integral mounting of the plurality of protrusions of the connecting structure on the exterior of the access engaging portion facilitates an at least minimal forced inward movement of the plurality of protrusions, because of the flexure of the remainder of an access engaging portion. More specifically, as the protrusions engage or the threads or surface 3' of the attachment structure surrounding the nozzle tube 2', a substantially "snap-action" occurs as the protrusions are forced over the threads or ribs of the attachment structure 3' due to the exertion of the linear pushing force on either the closure assembly or the syringe, as set forth above. As a result, the plurality of protrusions are forced over the threads, ribs or other connecting structures associated with the attachment structure of the nozzle or access portion. The forced snap-action of the protrusions and the threads of the attachment structure 3' thereby results in the aforementioned push-on connection. However, the remainder of the access engaging portion is sufficiently rigid or able to also permit a rotate-off disconnection or an "un-threading" of the plurality of protrusions from the thread-like structure defining the attachment structure of the nozzle or access portion of the syringe.

Further with regard to the flexible construction of the access engaging portion, a plurality of channels are formed in an outer wall thereof in adjacent, contiguous and/or communicating relation with corresponding ones of the living hinges. Moreover, the flexibility of the membranes or segments is attributable to the significantly reduced thickness thereof, when compared to the remainder of the outer wall of the access engaging portion. Also, the hinge segments or membranes are disposed in segregating relation between the interior of the channel and the interior of the access engaging portion. Therefore, when the push-on connection is attempted sufficient flexure will be developed in the access engaging portion to force the aforementioned "snap-action" of the plurality of protrusions as they are forced over the threaded or ribbed surface of the attachment structure 3' of the syringe 11.

As set forth above, the closure cap or closure cap or syringe cap of the present invention demonstrates sufficient structural versatility to be used alone, as a single closure and flow restrictor for the discharge port 4 of the syringe 11. However, the closure cap or closure cap or syringe cap may also be used in combination with an end cap and included indicator member and thereby serve as a tamper evident cap (TEC).

The end cap comprises a substantially hollow interior having an annular indicator member fixedly but removably secured therein by virtue of at least one but preferably a plurality of frangible attachment members. When used in combination with the end cap, the closure cap or closure cap or syringe cap is movably retained within the hollow interior of the end cap by virtue of it being disposed between the annular indicator member and the closed end portion of the end cap. Additional cooperative structuring of the closure cap or closure cap or syringe cap and the end cap may include a "cliff and ramp" type of connection and/or structure. Interaction of the "cliff and ramp" connectors on both the closure cap or closure cap or syringe cap and the closed end of the end cap will provide for concurrent rotation of the end cap and closure cap or closure cap or syringe cap in a single direction. Therefore, when used in combination with the end cap, the closure cap or closure cap or syringe cap may be rotationally or threadedly attached to the attachment structure 3' of the nozzle or access portion 2 of a syringe 11. However, due to the fact that the closure cap or closure cap or syringe cap is movable and not fixed within the interior of the end cap, the closure cap or closure cap or syringe cap cannot be rotated with the end cap in an opposite direction. Accordingly, the combination of the end cap and closure cap or closure cap or syringe cap, used as a TEC, will still allow for the "push-on" connection of the closure cap or closure cap or syringe cap with the attachment structure 3', while providing the additional versatility of being able to concurrently rotate the end cap and closure cap or closure cap or syringe cap in the aforementioned single direction to accomplish a "rotate-on" connection.

Access to the interior contents of the syringe 11 is then accomplished by forced removal, such as by a pulling force exerted on the end cap, serving to expose the closure cap or closure cap or syringe cap still attached to the nozzle or access portion 2 of the syringe 11. Such removal of the end cap in this manner will reveal the indicator member being effectively sandwiched between the closure cap or closure cap or syringe cap and the end of the syringe 11. The indicator member will thereby provide a clear visual indication that attempted access to the contents of the syringe, either authorized or unauthorized, has been made.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
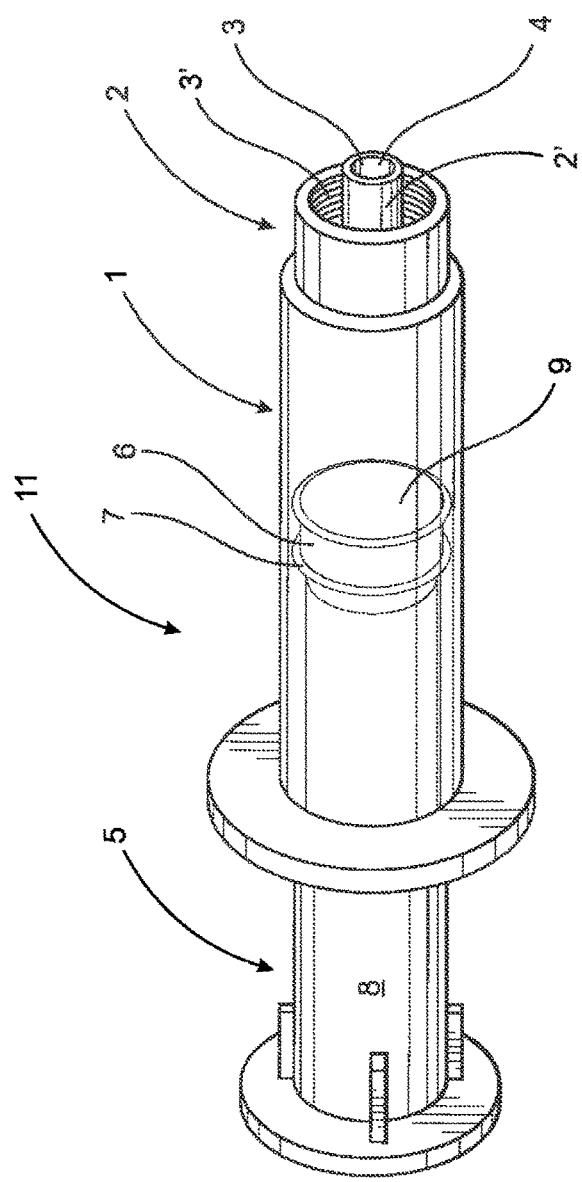
FIG. 1 is a view of a prior art syringe structure of the type with which the closure assembly of the present invention can be and/or is intended for use.
Figure 2:
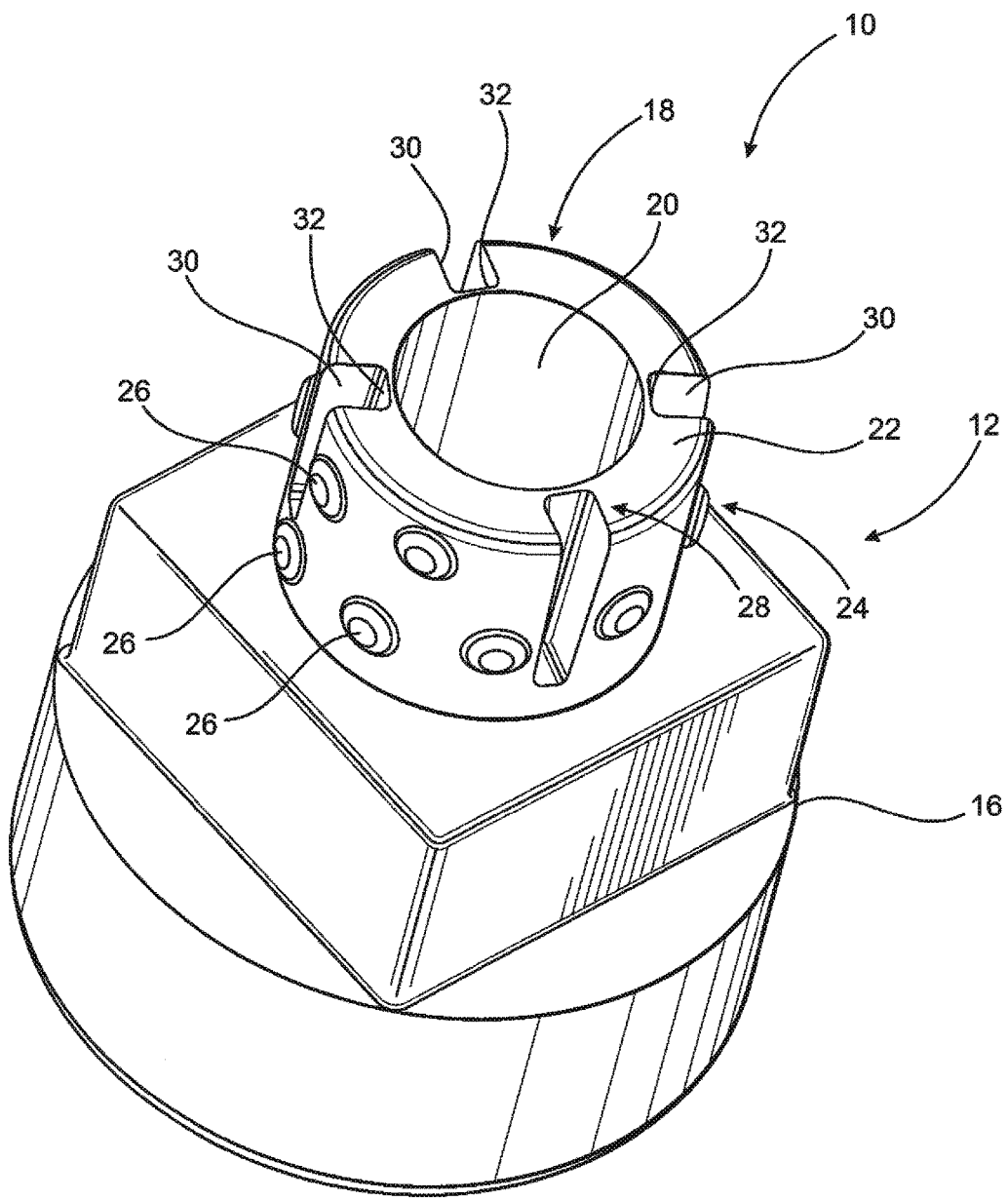
FIG. 2 is a perspective view of a closure cap or closure cap or syringe cap portion according to the inventive closure assembly described herein.
Figure 3:
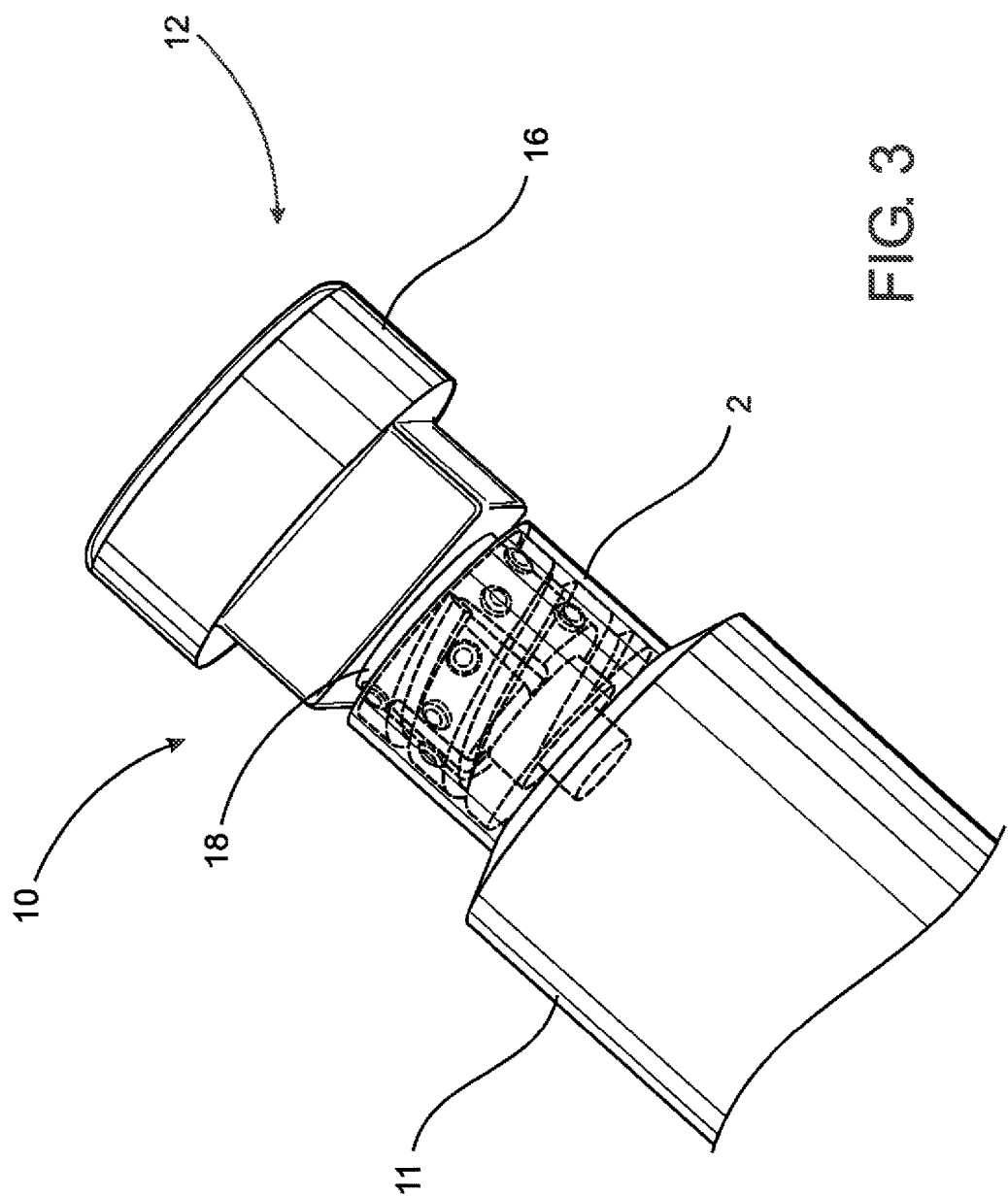
FIG. 3 is a perspective view of the closure cap or closure cap or syringe cap portion attached to a nozzle or access portion of the syringe of the type represented in FIG. 1, in flow restricting relation to the discharge port thereof.
Figure 4:
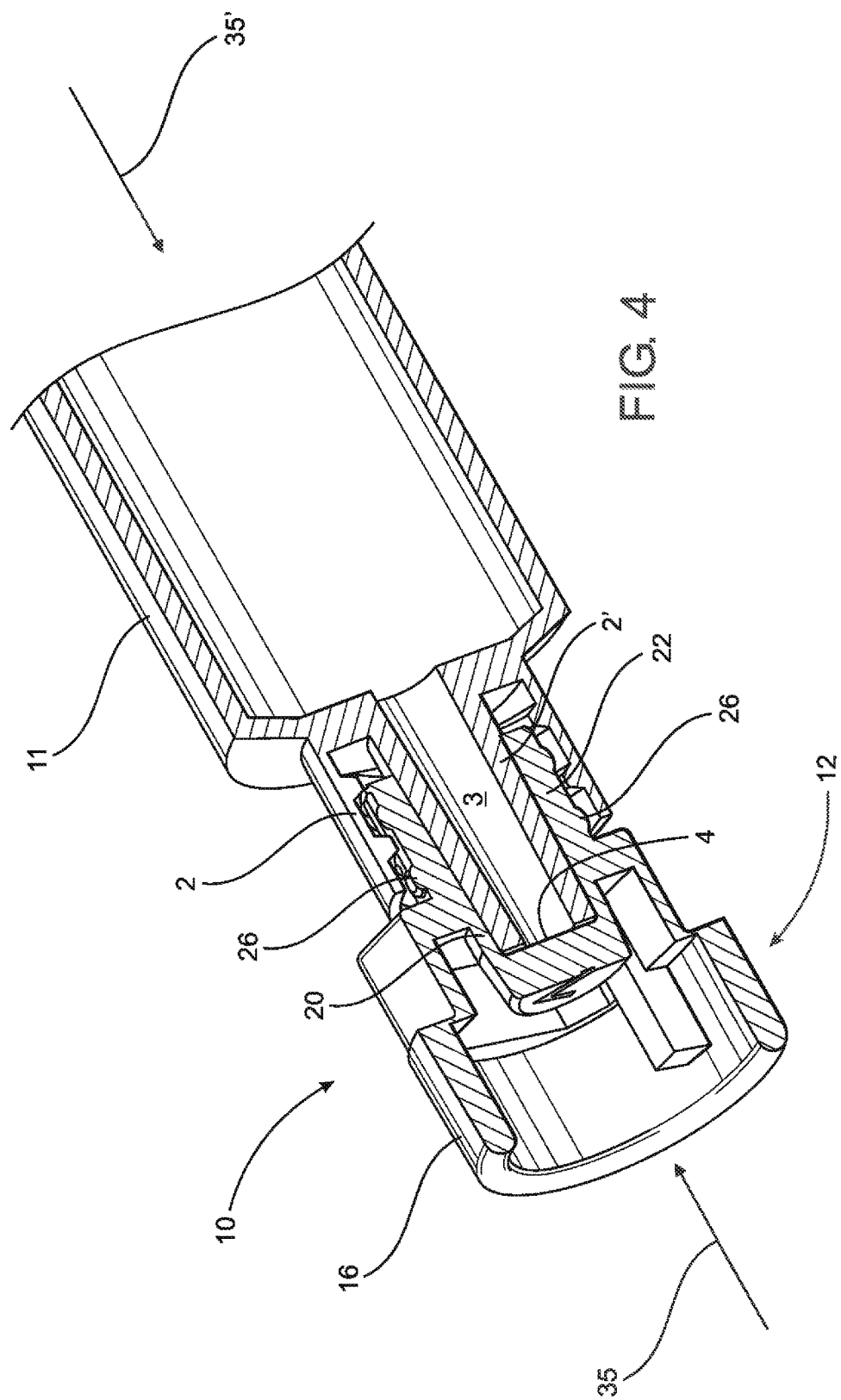
FIG. 4 is an interior sectional view of the closure cap or closure cap or syringe cap portion connected to the nozzle or access portion of the syringe as generally represented in FIG. 3.
Figure 5:
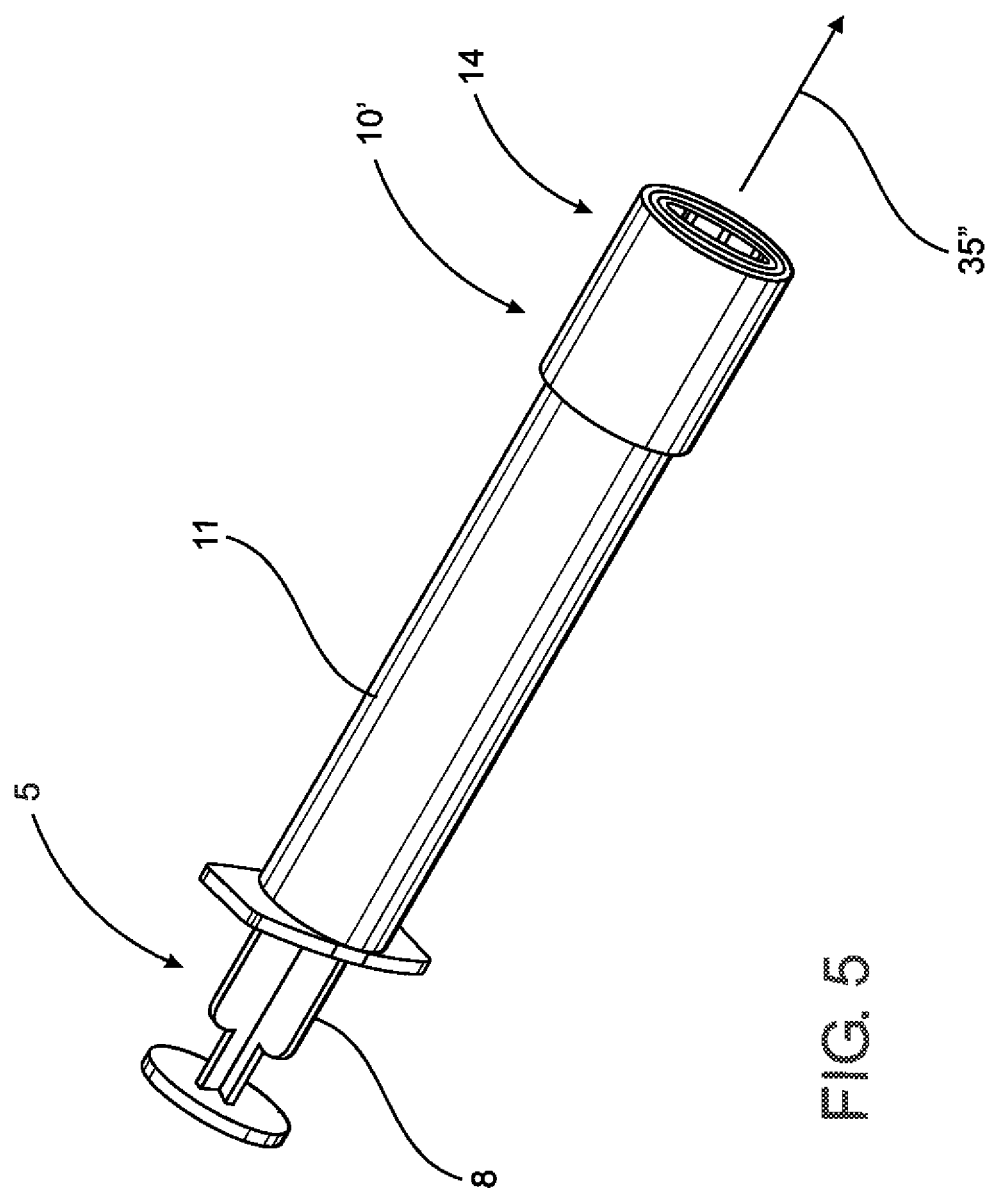
FIG. 5 is a perspective view of the closure assembly of the present invention including an end cap and thereby defining a tamper evident cap assembly.

As shown in the accompanying drawings, the present invention is directed to a closure assembly generally indicated as 10 in the embodiment of FIGS. 2-4 and generally indicated as 10' in the embodiment of FIGS. 5-6, 8 and 9. Both embodiments of the closure assembly 10 and 10' are structured for connection to a syringe 11, such as the type represented in FIG. 1 and labeled as "Prior Art." However, it is emphasized that the closure assembly 10, 10' of the present invention may be used with a variety of different medical containers or like medical devices in which a fluid is or may be stored and/or retained and which includes an access portion and a discharge port through which a contained fluid may be dispensed. Accordingly, the closure assembly 10, 10' is intended for use with a medical device, container such as, but not limited to, the syringe 11 having a nozzle or access portion 2 and a discharge port 4 associated with an interior channel 3 of the nozzle or access portion tube 2', which communicates with the interior of a barrel 1 of the syringe 11.

The various structural and operative features of the closure assembly 10 facilitate its versatility by including a closure cap or closure cap or syringe cap generally indicated as 12, which may also be referred to at times herein as a closure cap or closure cap or syringe cap portion. The closure cap or closure cap or syringe cap 12 is structured to be used independently in connection with a syringe 11, in flow restricting relation to the nozzle or access portion 2, and in particular, to the discharge port 4. However, the closure cap or closure cap or syringe cap 12 of the closure assembly 10' may also be used in combination with an end cap, generally indicated as 14 in FIGS. 5-6, 8 and 9, thereby enabling the closure assembly 10' to be used as a tamper evident cap (TEC).

First, and with primary reference to FIGS. 2 through 4, the closure assembly 10 comprises the closure cap or closure cap or syringe cap 12 including a base or body portion 16 having an integrally or fixedly secured access engaging portion 18. The access engaging portion 18 includes an at least partially hollow interior 20 dimensioned and configured to receive the discharge port 4 and nozzle or access portion tube 2' of a syringe therein, such as syringe 11 in FIG. 1. As set forth above, when in the connected orientation of FIGS. 3 and 4 the closure cap or closure cap or syringe cap 12 will enclose the nozzle or access portion tube 2' and the discharge port 4 in flow restricting relation thereto. As a result, the contents of the syringe 11, which are typically pre-loaded, will be prevented from passing out through the discharge port 4. Moreover, in at least one preferred embodiment, the exterior surface of the nozzle or access portion tube 2' of a syringe as shown in FIG. 1, and the surface on the open or hollow interior 20 of the closure cap or syringe cap 12 are cooperatively configured to define a "luer connection" or fitting. In addition, the closure cap or syringe cap 12 and more specifically, the access engaging portion 18 includes an outer cylindrical or other appropriately shaped wall 22 disposed in surrounding relation to the interior 20 and at least partially defines the boundaries thereof.

The aforementioned operative versatility of the closure assembly 10 and/or 10' is due at least in part to a connecting structure, which is generally indicated as 24 in FIG. 2. More specifically, and as is perhaps best shown in FIGS. 2 and 3, the connecting structure 24 comprises in the preferred embodiments a plurality of protrusions 26, each extending outwardly from the exterior surface of the outer wall 22 on the closure cap or syringe cap 12. Further, the plurality of protrusions 26 are ideally disposed collectively in an array having a predetermined configuration. Moreover, the predetermined configuration of the plurality of protrusions 26 is such as to facilitate a different type connection to and disconnection from the attachment structure 3' of the nozzle or access portion 2 of the syringe 11, such as that shown in FIG. 1. In at least one embodiment, the attachment structure 3' of the syringe 11 includes an interior surface that is at least partially ribbed or threaded. As such, the predetermined configuration of the plurality of protrusions 26 collectively comprise a substantially helical or other similar configuration which facilitates a rotational, threaded interactive engagement between the protrusions 26 and the attachment structure 3' of the syringe 11 to which the closure cap or syringe cap 12 is to be connected.

In addition, structural features which further facilitate the aforementioned different types of connection/disconnection of the closure cap or syringe cap to the nozzle or access portion 2 include the access engaging portion 18 and more specifically, the outer wall 22 having a "flexible construction." In at least one preferred embodiment, this flexible construction comprises at least one hinge, generally indicated as 28 in FIG. 2, formed in the outer wall 22 of the closure cap or syringe cap. However, the flexible construction of the access engaging portion 18 may also be defined by a plurality of hinges 28, each integrally formed in the outer wall 22 in spaced relation to one another as best represented in FIG. 2. In more specific terms, at least one but preferably each of the plurality of hinge structures 28 is defined by a "living hinge".

Moreover, each living hinge 28 preferably comprises an elongated channel 30 integrally formed in the outer wall 22 of the closure cap or syringe cap 12, such that an open side of each channel 30 is exposed to the exterior of the outer wall 22. Each living hinge 28 will preferably further comprise a hinge membrane or hinge segment 32 of reduced thickness when compared to the thickness of the outer wall 22. Practical ranges of the thickness of each of the hinge segments or membranes range from generally about 0.25 mm to 0.5 mm. However, it is emphasized that dimensional parameters of the hinge segments 32 may vary dependent upon the degree of flexure intended to be demonstrated by the outer wall 22 and/or the access engaging portion 18.

Therefore, the connecting structure comprising the plurality of protrusions 26 arranged in a predetermined array in combination with the flexible construction of the access engaging portion 18 provide a divergent connection/disconnection of the closure cap or syringe cap 12 onto the nozzle or access portion 2 and nozzle or access portion tube 2' of the syringe 11.

In more specific terms, the connecting structure 24 in combination with the flexible construction of the outer wall 22 of the access engaging portion 18 facilitate an "interactive engagement" with the attachment structure 3' of the syringe 11. Such interactive engagement comprises and enables a "push-on" connection of the closure cap or syringe cap onto the nozzle or access portion 2 as well as a "rotate-off" disconnection of the closure cap or syringe cap 12 from the nozzle or access portion 2. The push-on connection may be more specifically defined by an axial alignment between the nozzle or access portion tube 2' and the hollow interior 20 of the access engaging portion 18. Once such an axial alignment is accomplished, a substantially linearly directed force may be exerted on either the closure cap or syringe cap 12 or the syringe 11 in the manner schematically represented as 35 and 35' respectively in FIG. 4. In contrast, the rotate-off disconnection of the closure cap or syringe cap 12 from the nozzle or access portion 2 is accomplished by a relative rotational engagement between the closure cap or syringe cap 12 and the attachment structure 3' of the nozzle or access portion 2.

With further regard to the aforesaid "push-on" connection, the fixed or integral mounting of the plurality of protrusions 26 on the exterior of the access engaging portion 18 facilitates at least a minimal, radially inward displacement of the plurality of protrusions 26 with the outer wall 22, because of the flexible construction of the access engaging portion 18 and resulting flexure of the outer wall 22, as set forth above. More specifically, as the protrusions 26 are forced transversely over the threads or ribs of the attachment structure 3', a "snap-fit" type of action occurs there-between due to the exertion of the linear pushing force 35 and/or 35' on either the closure assembly 10 or the syringe 11, as set forth above. As a result, the plurality of protrusions 26 are concurrently forced over the threads or ribs on the attachment structure 3' and flexed, at least minimally, radially inward along with the outer wall 22. This forced "snap-fit" action between the protrusions 26 and the threads of the attachment structure 3' results in the aforementioned push-on connection.

However, in order to maintain a secure connection between the closure cap or syringe cap 12 and the nozzle or access portion 2 and discharge port 4, a rotate-off disconnection is provided. Accordingly, once the closure cap or syringe cap 12 is mounted in the operative position, as represented in FIG. 4, a rotational interactive engagement between the protrusions 26 and the threaded or ribbed surface of the attachment structure 3' facilitates the aforementioned rotate-off disconnection.

While the aforementioned push-on or snap-on connection and the rotate-off disconnection may be preferred in many practical applications, the versatility of the closure cap or syringe cap 12 also facilitates the ability to perform a "rotate-on" connection of the closure cap or syringe cap 12 with the nozzle or access portion 2. Accordingly, the aforementioned interactive engagement between the connecting structure 24 and the attachment structure 3' provides for a rotate-on connection and a rotate-off disconnection, as well as the push-on connection and rotate-off disconnection in the manner described above.

Figure 6:
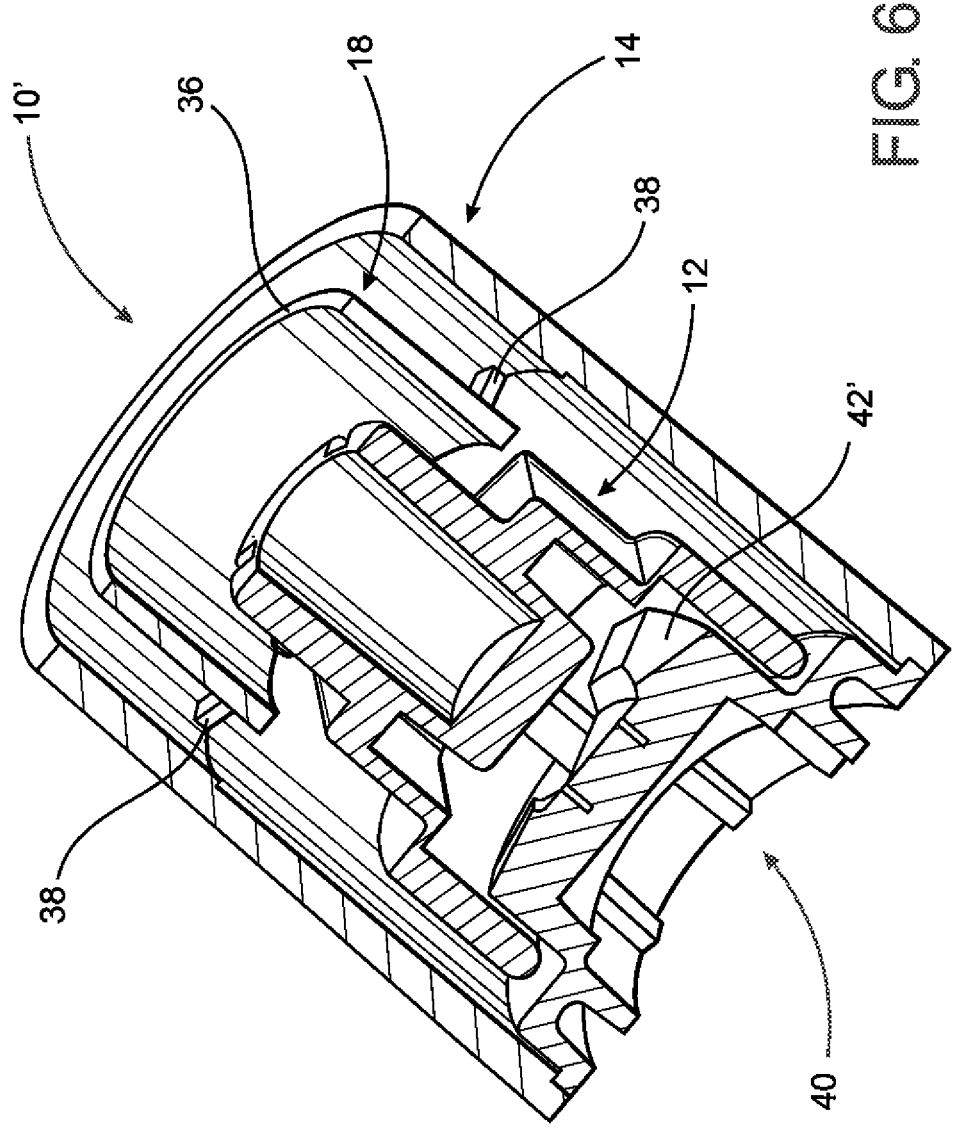
FIG. 6 is a perspective interior sectional view of the closure cap or closure cap or syringe cap portion and end cap when used in combination with one another.
Figure 7:
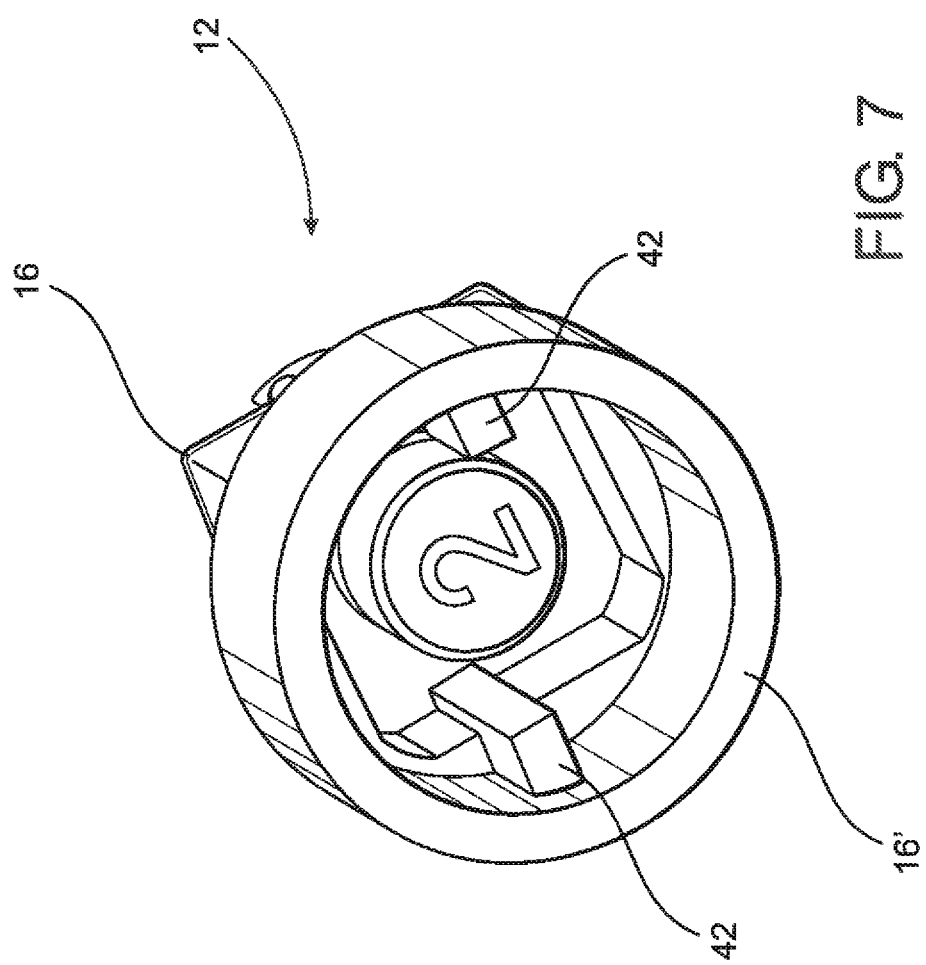
FIG. 7 is a bottom perspective view of the closure cap or closure cap or syringe cap portion.
Figure 8:
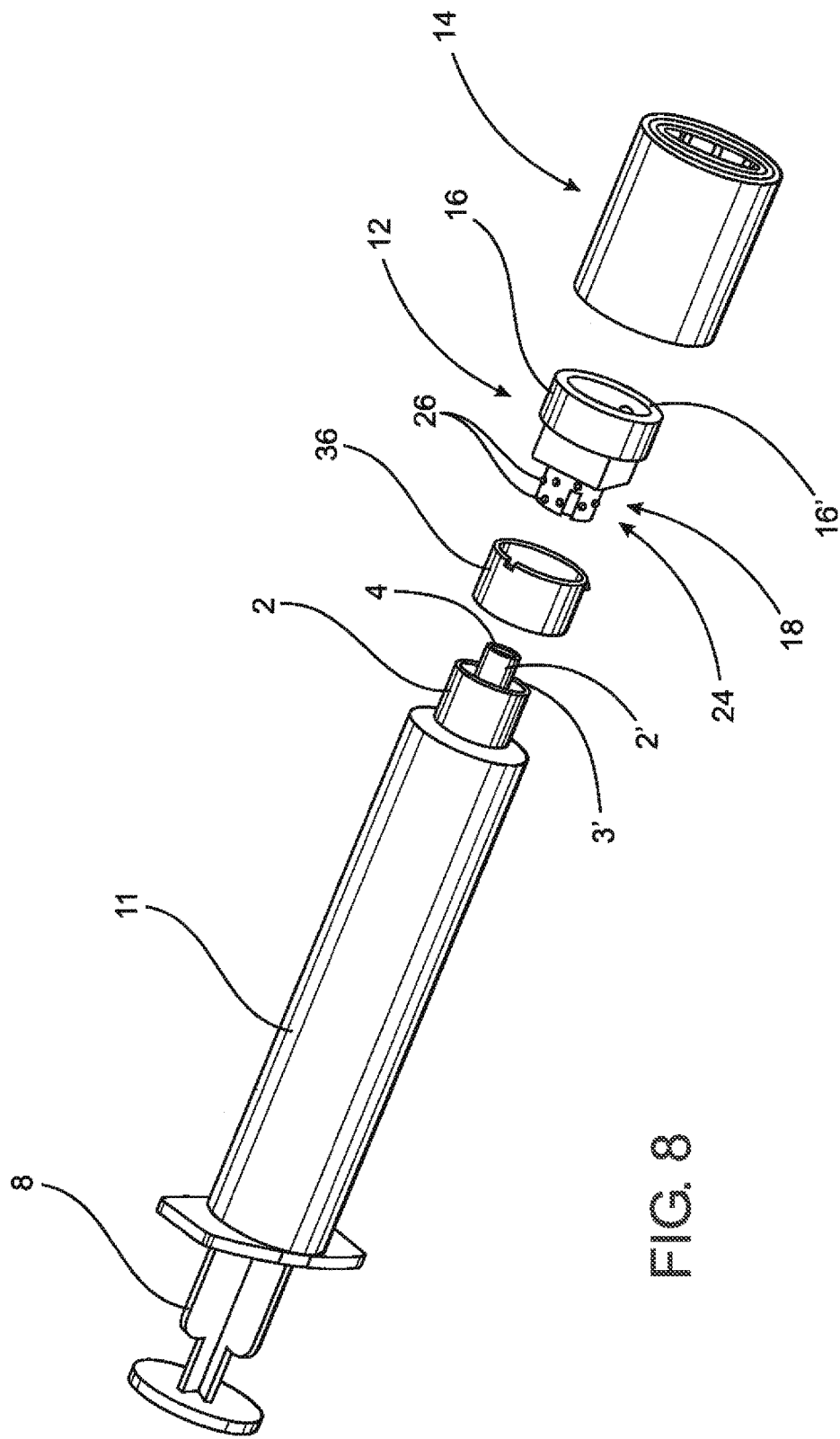
FIG. 8 is a perspective view in exploded form of the various components of the embodiment of FIGS. 5 and 6.
Figure 9:
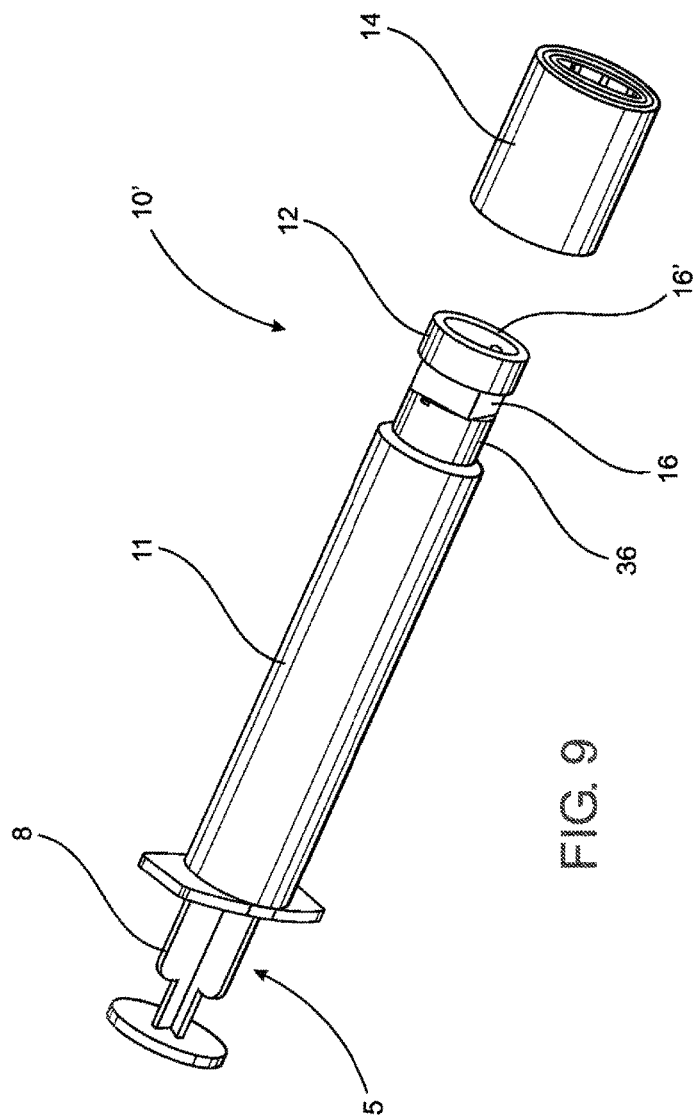
FIG. 9 is a perspective view of the embodiment of FIG. 5 with the end cap removed from the syringe and closure cap or closure cap or syringe cap.
Figure 10:
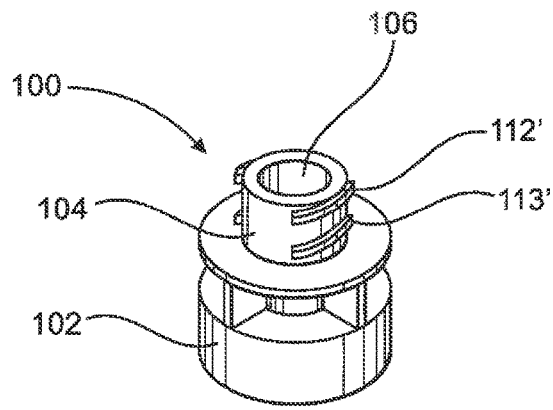
FIG. 10 is a perspective view of yet another preferred embodiment of the closure assembly of the present invention.
Figure 11:
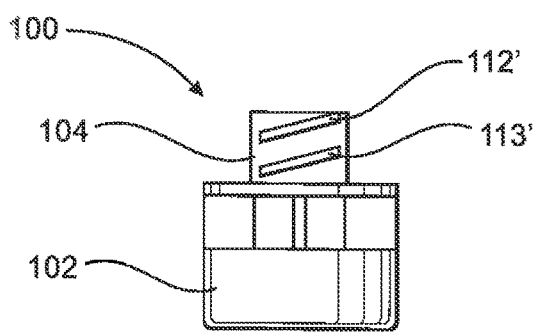
FIG. 11 is a front view of the embodiment of FIG. 10.
Figure 12:
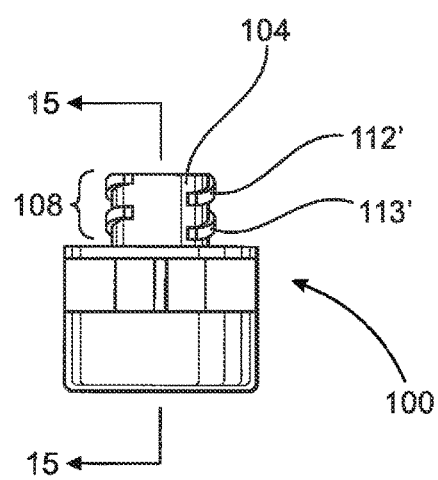
FIG. 12 is a side view of the embodiment of FIG. 10.
Figure 13:
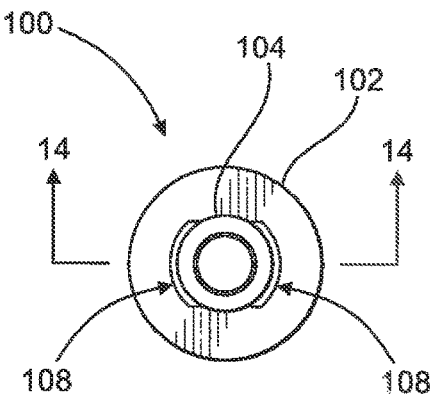
FIG. 13 is a top view of the embodiment of FIG. 10.

As set forth above, and as specifically represented in FIG. 5 through 9, the closure cap or syringe cap 12 may be used by itself or in combination with an end cap 14. When the closure cap or syringe cap 12 and the end cap 14 are used in combination, the closure cap or syringe cap 12 is loosely or movably disposed within an at least partially hollow interior of the end cap 14 and is not fixedly connected to interior portions of the end cap 14. As also represented in FIG. 6, the end cap 14 includes an indicator ring or member 36. Depending upon the structural and operative features of the end cap 14 the indicator ring or member 36 may be initially but removably fixed to the interior surfaces of the end cap 14 by at least one, but preferably a plurality of frangible members 38. In the alternative, the indicator ring it may be attached to the exterior of the closure or syringe cap 12. Therefore, when initially assembled the closure cap or syringe cap 12 is movably retained between a closed end portion 40 of the end cap 14 (see FIG. 6) and the fixedly but removably connected indicator member 36. It is further emphasized that the end cap 14 is representative only of a variety of different end cap structures with which the closure or syringe cap 10, 10', etc. may be used to define a TEC Cooperative structuring between the closure cap or syringe cap 12 and the end cap 14 is further demonstrated in FIGS. 6 and 7. More specifically, an open interior end generally indicated as 16' of the base or body portion 16 provides access to a "ramp and cliff" type connection generally indicated as 42. The ramp and cliff connection 42 is cooperatively dimensioned, disposed and structured to operatively engage a corresponding "ramp and cliff" connecting structure 42' integrally or fixedly attached to the closed end 40 of the end cap 14. Interactive engagement between the cliff and ramp connections 42 and 42' allow concurrent rotation of the closure cap or syringe cap 12, with the end cap 14 only in a single direction. When so rotated, a closure cap or syringe cap may be rotationally attached to the attachment structure 3' of the nozzle or access portion 2 by virtue of the above noted "rotate-on connection". However, it is emphasized that the above noted and preferred "push-on connection" of the closure cap or syringe cap onto the nozzle or access portion 2, can also be accomplished when the closure cap or syringe cap 12 is used in combination with the end cap 14 in the manner assembled in FIG. 6. Accordingly, the cliff and ramp connections 42 and 42' will allow a concurrent rotation of the closure cap or syringe cap 12 with the end cap 14, as long as the end cap 14 is rotated in a single, predetermined direction. Attempted rotation of the end cap 14 in the opposite direction will result in "slippage" of the closure cap or syringe cap 12 relative to the closed end 40. This will prevent a rotate-off disconnection of the closure cap or syringe cap 12 relative to the nozzle or access portion 2, as long as the end cap 14 remains in place.

Based on the above, authorized or non-authorized attempted access to the syringe 11, and more specifically, to the contents thereof, is indicated by forced removal of the end cap 14 from the closure cap or syringe cap 12. Such a forced removal may be accomplished by a pulling force, schematically indicated as 35" in FIG. 5, being exerted on the end cap 14. Such a pulling force 35" will result in a breakage of the frangible members 38 and the resultant indicating placement of the indicator member 36 on the syringe 11, in the manner represented in FIG. 9. As a result, subsequent observation of the syringe 11 once the end cap 14 has been removed will clearly indicate that an attempted access, either authorized or unauthorized, to the syringe 11 and its contents have been attempted. Once the end cap 14 is disconnected, closure cap or syringe cap 12 can thereby be rotationally manipulated or positioned to accomplish the aforementioned "rotate-off disconnection" of the closure cap or syringe cap 12 from the nozzle or access portion 2 in order to provide unobstructed access to the contents on the interior of the syringe 11.

Therefore, the closure assembly 10 and 10' of the present invention provides a unique structure capable of connecting the closure cap or syringe cap 12, whether used independently or in combination with the end cap 14, by means of a "push-on connection" and a "rotate-off disconnection". In addition, interactive rotational engagement between the plurality of protrusions 26 of the connector structure 24 facilitates a "rotate-on connection" and a "rotate-off disconnection" of the closure cap or syringe cap 12 and the nozzle or access portion 2.

Yet another preferred embodiment of the present invention is represented in FIGS. 10 through 17, wherein the closure assembly is generally indicated as 100. Moreover, the closure assembly 100 is also structured to be operatively connected to an access portion of a medical device/container which may or may not be in the form of a syringe or pre-filled syringe 11 as represented in FIG. 1 above.

More specifically, the closure assembly 100 includes a closure cap 102 having an access receiving portion 104. The interior 106 of the access receiving portion 104 includes a tapered configuration which may be in the form of or at least partially define a Luer fitting and/or a female Luer fitting. Such Luer fitting is dimensioned to receive the access portion tube 2' of the syringe 11 or other type medical device/container therein in flow restricting relation to a discharge port 4 thereof. In addition, the access receiving portion 104 includes a segmented threaded structured generally indicated as 108 on the exterior surface thereof. The segmented thread structure 108 may be structurally distinguishable from but operatively similar to the segmented thread structure comprising the plurality of protrusions 26 formed on the exterior of the access engaging portion of the embodiments of FIGS. 2 through 9. As such, the plurality of protrusions 26 have a generally circular or curvilinear outer peripheral configuration which define a segmented thread structure.

However, the segmented thread structure 108 in the embodiment of FIGS. 10 through 17 include a plurality of protrusions 112 and 113 respectively defining an outer most thread section and an inner most read section. Further, each of a plurality of thread segments defining both the outer thread section 112 and the inner thread section 113 comprises a substantially elongated configuration extending in spaced relation to one another along the length of the respective outer thread section 112 an inner thread section 113. In addition each or at least some of the plurality of thread segments 112' have a smaller overall dimension then each or at least some of the plurality of thread segments 113', which define the inner thread section 113. A comparison of FIGS. 16 and 17 clearly indicates the dimensional differences between the thread segments 112' and 113', as well as the difference in the distances which the respective thread segments 112' and 113' protrude outwardly from the exterior surface of the access engaging portion 104.

More specifically, the plurality of thread segments 112' defining the outer thread section 112 extend outwardly from the outer surface of the access receiving portion 104 a lesser distance than that of each of the thread segments 113', defining the inner thread section 113. Moreover, the dimension and outwardly protruding distance of each of the thread segments 112' is such as to facilitate an axial, linearly directed, overlapping, sliding engagement of the attachment structure 3' and the threads or ribs associated therewith, as being part of the access portion 2 of the syringe or medical container/device. As a result, the aforementioned push-on connection will be accomplished by the attachment structure 3' moving linearly in overlapping, sliding or confronting engagement with the plurality of lesser dimensioned thread segments 112' defining the outer thread section 112. In contrast, the larger dimension of the thread segments 113' of the inner thread section 113 is such that the thread segments 113' extend outwardly from the outer surface of the access receiving portion 104 a greater distance than the thread segments 112', as set forth above. As a result, the linear movement and overlapping, sliding engagement of the attachment structure 3' of the access portion 2 will contact and/or engage the outwardly protruding thread segments 113' and thereby be prevented or restricted from being axially forced or moved in overlapping relation thereto. Instead, connection between the attachment structure 3' and the inner thread section 113 may be accomplished by a rotational, threaded engagement. Such a rotational, threaded engagement may further accomplish a rotate-off disconnection or a rotate-on connection of the attachment structure 3' of the access structure 2 with the segmented thread structure 108.

Therefore, the closure assembly 100 is structured to facilitate an interactive engagement comprising a rotate-off disconnection of the closure cap 102 from the access portion 2 and/or attachment structure 3' associated therewith. In addition, the closure assembly 100 is structured to further define the interactive engagement including an at least partial push-on connection between the closure 102 and the access portion 3', in the manner described above with regard to the embodiment of the closure assembly 10, 10' as represented in FIGS. 2 through 9. In more specific terms, the rotate-off disconnection comprises relative rotational engagement between the closure cap 102 and the attachment structure 3' of the access portion 2. Further, the push-on connection is at least partially defined by an axial alignment between the access portion 2 and/or attachment structure 3' and the closure cap 102 as well as the segmented thread structure 108.

As also described above, the push-on connection is accomplished primarily between the access portion 2 and associated attachment structure 3' being linearly disposed in overlapping, sliding engagement with the thread segments 112' of the upper thread section 112. This push-on connection is further facilitated by at least a minimal amount of flexure of the access receiving portion 104 due to its being formed, at least in part, from an inherently flexible material such as, but not limited to, polypropylene.

As set forth above, and as specifically represented in FIG. 5 through 9, the closure cap or syringe cap 102 may be used by itself or in combination with an end cap 14. When the closure cap or syringe cap 102 and the end cap 14 are used in combination, the closure cap or syringe cap 102 is loosely or movably disposed within an at least partially hollow interior of the end cap 14 and is not fixedly connected to interior portions of the end cap 14. As also represented in FIG. 6, the end cap 14 may include an indicator ring or member 36. Depending upon the structural and operative features of the end cap 14 the indicator ring or member 36 may be initially but removably fixed to the interior surfaces of the end cap 14 by at least one, but preferably a plurality of frangible members 38. In the alternative, the indicator ring it may be similarly attached to the exterior of the closure or syringe cap 102. Therefore, when initially assembled the closure cap or syringe cap 102 is movably retained between a closed end portion 40 of the end cap 14 (see FIG. 6) and the fixedly but removably connected indicator member 36. It is further emphasized that the end cap 14 is representative only of a variety of different end cap structures with which the closure or syringe cap 10, 10', etc. may be used to define a TEC.

Figure 14:
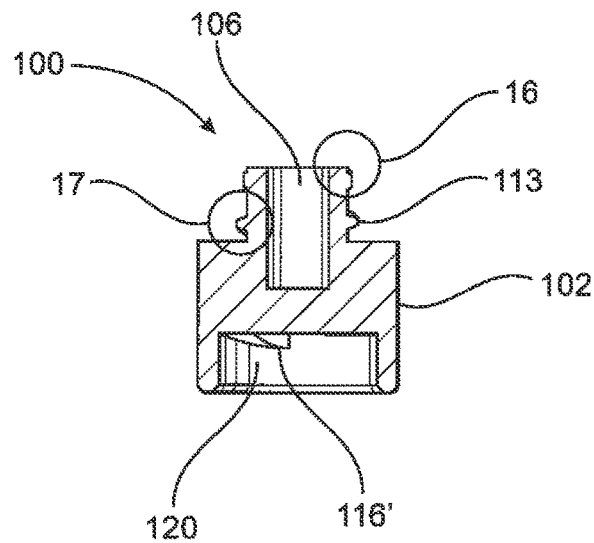
FIG. 14 is a sectional view along line 14-14 of FIG. 13.
Figure 15:
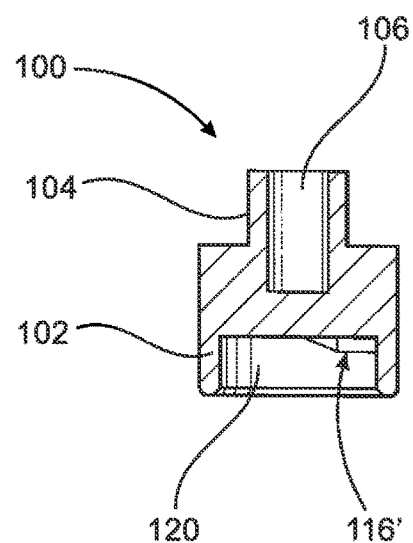
FIG. 15 is a sectional view along line 15-15 of FIG. 12.
Figure 16:
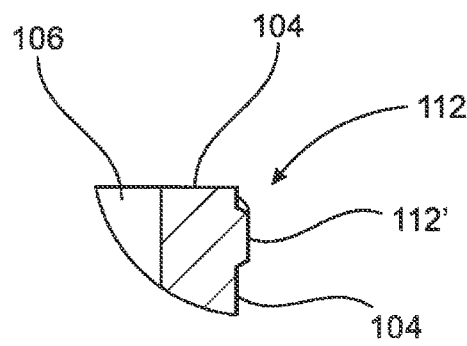
FIG. 16 is a detail view of the indicated portion of FIG. 14.
Figure 17:
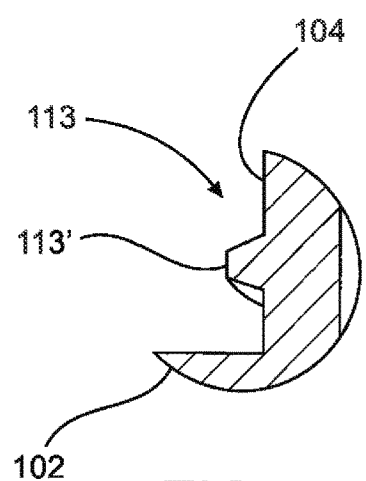
FIG. 17 is a detail view of the indicated portion of FIG. 14.

Cooperative structuring between the closure cap or syringe cap 102 and the end cap 14 is further demonstrated in FIGS. 14 and 15. More specifically, an open ended interior end generally indicated as 116' of the base or body portion 116 provides access to a "ramp and cliff" type connection generally indicated as 120. The ramp and cliff connection 120 is cooperatively dimensioned, disposed and structured to operatively engage a corresponding "ramp and cliff" connecting structure 42' integrally or fixedly attached to the closed end 40 of the end cap 14. Interactive engagement between the cliff and ramp connections 120 and 42' allow concurrent rotation of the closure cap or syringe cap 102, with the end cap 14 only in a single direction. When so rotated, the closure cap or syringe cap may be rotationally attached to the attachment structure 3' of the nozzle or access portion 2 by virtue of the above noted "rotate-on connection". However, it is emphasized that the above noted and preferred "push-on connection" of the closure cap or syringe cap 102 onto the nozzle or access portion 2, can also be accomplished when the closure cap or syringe cap 102 is used in combination with the end cap 14 in the manner assembled in FIG. 6. Accordingly, the cliff and ramp connections 120 and 42' will allow a concurrent rotation of the closure cap or syringe cap 102 with the end cap 14, as long as the end cap 14 is rotated in a single, predetermined direction. Attempted rotation of the end cap 14 in the opposite direction will result in "slippage" of the closure cap or syringe cap 102 relative to the closed end 40. This will prevent a rotate-off disconnection of the closure cap or syringe cap 102 relative to the nozzle or access portion 2, as long as the end cap 14 remains in place.

Based on the above, authorized or non-authorized attempted access to the syringe 11, and more specifically, to the contents thereof, is indicated by forced removal of the end cap 14 from the closure cap or syringe cap 102. Such a forced removal may be accomplished by a pulling force, schematically indicated as 35" in FIG. 5, being exerted on the end cap 14. Such a pulling force 35" may result in a breakage of the frangible members 38 and the resultant indicating placement of the indicator member 36 on the syringe 11, in the manner represented in FIG. 9. As a result, subsequent observation of the syringe 11 once the end cap 14 has been removed will clearly indicate that an attempted access, either authorized or unauthorized, to the syringe 11 and its contents have been attempted. Once the end cap 14 is disconnected, closure cap or syringe cap 102 can thereby be rotationally manipulated or positioned to accomplish the aforementioned "rotate-off disconnection" of the closure cap or syringe cap 102 from the nozzle or access portion 2 in order to provide unobstructed access to the contents on the interior of the syringe 11.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A closure assembly for a medical device having an access portion with a discharge port, said closure assembly comprising:
    a closure cap including an access engaging portion removably connectible in flow restricting relation to the discharge port,
    a connecting structure mounted on said access engaging portion and disposed and configured to define an interactive engagement with an attachment structure of the access portion,
    said interactive engagement comprising an at least partial push-on connection of said closure cap to the access portion,
    said interactive engagement further comprising a rotate-off disconnection of said closure cap from said access portion,
    said connecting structure comprising a segmented thread structure formed on an exterior of said access engaging portion, said segmented thread structure having a predetermined configuration,
    said segmented thread structure comprising a plurality of spaced apart protrusions, and
    said segmented threaded structure further comprising at least an outer thread section and an inner thread section; said outer thread section cooperatively dimensioned with the attachment structure to facilitate an axial, linear movement and overlapping, sliding engagement therebetween; said axial, linear movement at least partially defining said push-on connection.

2. The closure assembly as recited in claim 1 wherein said push-on connection is at least partially defined by an axial alignment between the access portion and said closure cap and a relative, substantially linearly directed movement of either said closure cap or the medical device towards one another.

3. The closure assembly as recited in claim 2 wherein said rotate-off disconnection comprising relative rotational engagement between said closure cap and the attachment structure of the access portion.

4. The closure assembly as recited in claim 1 wherein said predetermined configuration of said segmented thread structure is substantially helical and cooperatively dimensioned with the attachment structure to facilitate a rotationally threaded engagement therebetween.

5. The closure assembly as recited in claim 4 wherein said threaded engagement further comprises a rotational threaded connection or a rotational threaded disconnection between said segmented thread structure and the attachment structure.

6. The closure assembly as recited in claim 5 wherein said push-on connection is at least partially defined by a substantially axial alignment between the access portion and said closure cap and a substantially linear movement of either said closure cap or the attachment structure toward and relative to one another.

7. The closure assembly as recited in claim 1 wherein said push-on connection further comprises a relative, substantially axial movement and sliding engagement of at least an outer portion of said segmented threaded structure and the attachment structure of the access portion.

8. The closure assembly as recited in claim 1 wherein said inner thread section comprises a larger dimension than said outer thread segment; said larger dimension sufficient to restrict said axial linear movement and overlapping, sliding engagement of the attachment structure relative to said inner thread section.

9. The closure assembly as recited in claim 8 wherein said inner and outer thread sections each comprise a plurality of spaced apart protrusions.

10. The closure assembly as recited in claim 9 wherein each of said plurality of protrusions comprises a substantially elongated configuration.

11. The closure assembly as recited in claim 9 wherein each of said plurality of protrusions comprises a substantially curvilinear peripheral configuration.

12. The closure assembly as recited in claim 1 wherein said plurality of protrusions comprise substantially elongated configurations.

13. The closure assembly as recited in claim 1 wherein said plurality of protrusions comprise substantially circular configurations.

14. The closure assembly as recited in claim 1 wherein said outer threaded section is formed on and extends outwardly, a predetermined distance, from an outer surface of said access engaging portion; said predetermined distance being sufficient to facilitate said axial linear movement and overlapping, sliding engagement between said attachment structure and said outer thread section.

15. The closure assembly as recited in claim 14 wherein said inner thread section comprises a larger dimension than said outer thread section; said larger dimension sufficient to restrict said axial linear movement and overlapping, sliding engagement between the attachment structure and said inner thread section.

16. The closure assembly as recited in claim 1 further comprising an end cap including an indicator member mounted on an interior of said end cap; said closure cap at least partially enclosed within said end cap.

17. The closure assembly as recited in claim 16 wherein said closure cap is movably retained within said end cap.

18. The closure assembly as recited in claim 16 wherein said closure cap and said end portion of said end cap are cooperatively disposed and structured to facilitate concurrent rotation of said closure cap and said end cap in only a single direction and a rotate-on connection of said closure cap on the attachment structure.

19. The closure assembly as recited in claim 18 wherein said connecting structure comprises a plurality of protrusions formed on an exterior of said access engaging portion; said plurality of protrusions collectively disposed into a predetermined configuration.

20. The closure assembly as recited in claim 19 wherein said interactive engagement further comprises a rotate-on connection of said closure cap and the attachment structure; said rotate-on connection at least partially defined by relative rotational engagement between said plurality of protrusions and the attachment structure of the access portion upon concurrent rotation of said end cap and said closure cap in said single direction.

21. The closure assembly as recited in claim 16 wherein said connecting structure comprises a plurality of protrusions collectively formed on an exterior of said access engaging portion into a predetermined configuration; said access engaging portion comprises a flexible construction sufficient to accomplish a predetermined flexure thereof; said plurality of protrusions movable with said access engaging portion during flexure thereof into connection with the attachment structure of the access portion during said push-on connection.

22. The closure assembly as recited in claim 21 wherein said flexible construction comprises a plurality of hinge structures; at least some of said plurality of hinge structures comprising a living hinge formed in an outer wall of said access engaging portion in spaced relation to one another.

23. The closure assembly as recited in claim 1 wherein an interior of said access engaging portion comprises a female Luer fitting dimensioned to receive the access portion therein in flow restricting relation to the discharge port thereof.

24. A closure assembly for a medical device having an access portion with a discharge port, said closure assembly comprising:
a closure cap including an access engaging portion removably connectible in flow restricting relation to the discharge port,
a connecting structure mounted on said access engaging portion and disposed and configured to define an interactive engagement with an attachment structure of the access portion,
said interactive engagement comprising an at least partial push-on connection of said closure cap to the access portion,
said interactive engagement further comprising a rotate-off disconnection of said closure cap from said access portion, and
said access engaging portion comprising a flexible construction sufficient to accomplish a predetermined flexure thereof at least during said push-on connection; said connecting structure movable with said access engaging portion during flexure thereof into connection with the attachment structure of the access portion during said push-on connection.

25. The closure assembly as recited in claim 24 wherein said flexible construction comprises at least one hinge formed on said access engaging portion.

26. The closure assembly as recited in claim 25 wherein said one hinge comprises a living hinge including a channel formed in said access engaging portion and a hinge segment of reduced thickness disposed in segregating relation between an interior of said channel and an interior of said access engaging portion.

27. The closure assembly as recited in claim 26 wherein said hinge segment is integrally formed on said access engaging portion and comprises a substantially lesser thickness than that of contiguous portions of said access engaging portion.

28. The closure assembly as recited in claim 24 wherein said flexible construction comprises a plurality of hinge structures; at least some of said plurality of hinge structures comprising a living hinge formed in an outer wall of said access engaging portion in spaced relation to one another.

29. The closure assembly as recited in claim 28 wherein each of said living hinges comprises a channel formed in said outer wall and a reduced thickness hinge segment integrally formed in said outer wall.

30. The closure assembly as recited in claim 29 wherein said reduced thickness hinge segment is disposed and structured to at least partially define a fluid flow barrier between an interior of said access engaging portion and an exterior thereof.

\* \* \* \* \*